US00PP19975P2

(12) United States Plant Patent
Shaw et al.

(10) Patent No.: US PP19,975 P2
(45) Date of Patent: May 12, 2009

(54) STRAWBERRY PLANT NAMED 'SAN ANDREAS'

(50) Latin Name: *Fragaria×ananassa*
Varietal Denomination: San Andreas

(75) Inventors: Douglas V. Shaw, Davis, CA (US); Kirk D. Larson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 53 days.

(21) Appl. No.: 12/011,335

(22) Filed: Jan. 25, 2008

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para
(74) *Attorney, Agent, or Firm*—Townsend and Townsend and Crew LLP

(57) ABSTRACT

This invention relates to a new and distinctive day-neutral type of strawberry designated as 'San Andreas'. 'San Andreas' is a day-neutral (everbearing) cultivar similar to 'Diamante' (U.S. Plant Pat. No. 10,435) but with higher yield and better quality fruit, better disease resistance and better flavor. It is similar to 'Albion' (U.S. Plant Pat. No. 16,228) for fruit quality but with higher yield, and larger and more attractive fruit.

3 Drawing Sheets

Genus and species:
The strawberry cultivar of this invention is botanically identified as *Fragaria ×ananassa* Duch.

Variety denomination: The variety denomination is 'San Andreas'.

BACKGROUND OF THE INVENTION

This invention relates to a new and distinctive day-neutral type cultivar designated as 'San Andreas', which resulted from a cross performed in 2001 between the cultivar 'Albion' (U.S. Plant Pat. No. 16,228) and advanced selection Cal 97.86-1. 'San Andreas' was first fruited at the University of California Wolfskill Experimental Orchard, near Winters, Calif. in 2002, where it was selected, originally designated Cal 1.139-2, and propagated asexually by runners. Following selection and during testing, the plant of this selection was designated 'CN223' and, later for introduction into commerce, 'San Andreas'. Asexual propagules from this original source have been tested at the Watsonville Strawberry Research Facility, the South Coast Research and Extension Center, and to a limited extent in grower fields starting in 2005.

BRIEF SUMMARY OF THE INVENTION

'San Andreas' is a day-neutral (everbearing) cultivar similar to 'Diamante' (U.S. Plant Pat. No. 10,435) but with higher yield and better quality fruit, better disease resistance and better flavor. It is similar to 'Albion' (U.S. Plant Pat. No. 16,228) for fruit quality but with higher yield, and larger and more attractive fruit.

BRIEF DESCRIPTION OF THE DRAWINGS

The figures depict various characteristics of the 'San Andreas' cultivar.

DETAILED DESCRIPTION OF THE INVENTION

Figure 1:
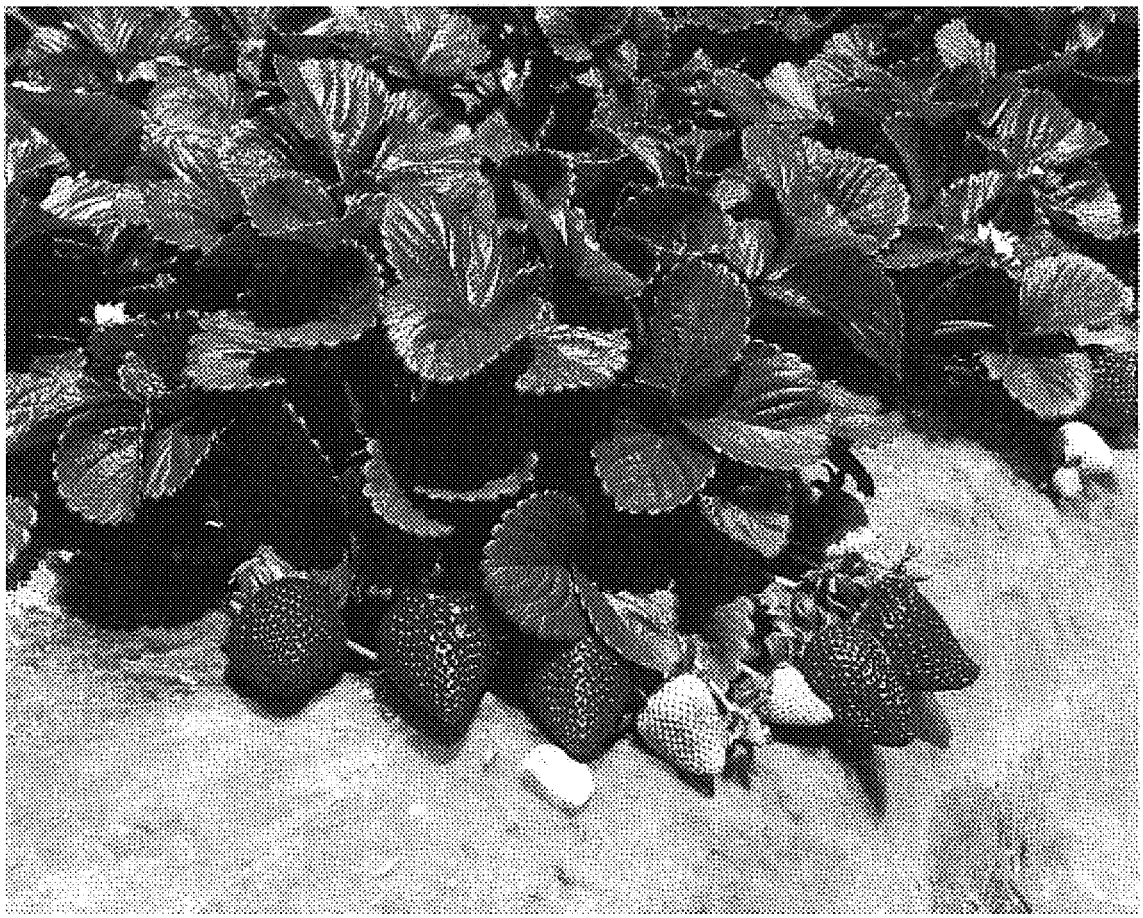
FIG. 1 shows the general flowering and fruiting characteristics of the plant in a field planting.
Figure 2:
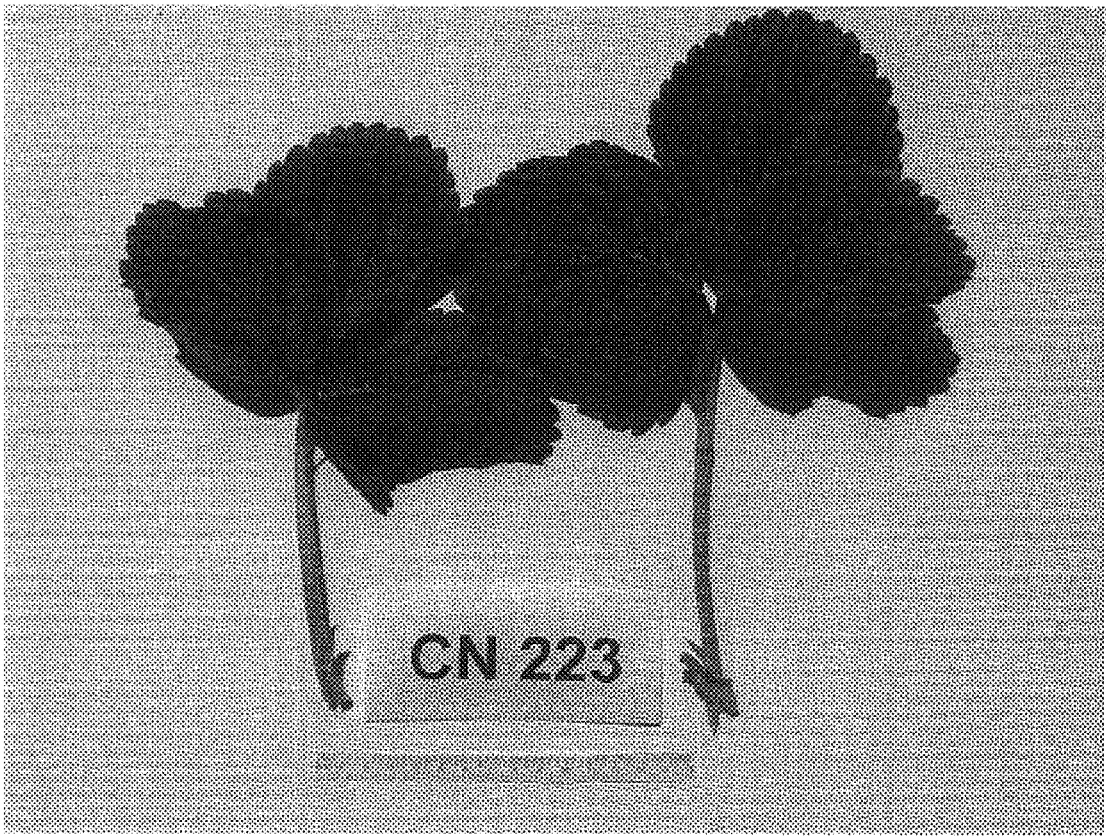
FIG. 2 shows a typical leaf at mid-season.
Figure 3:
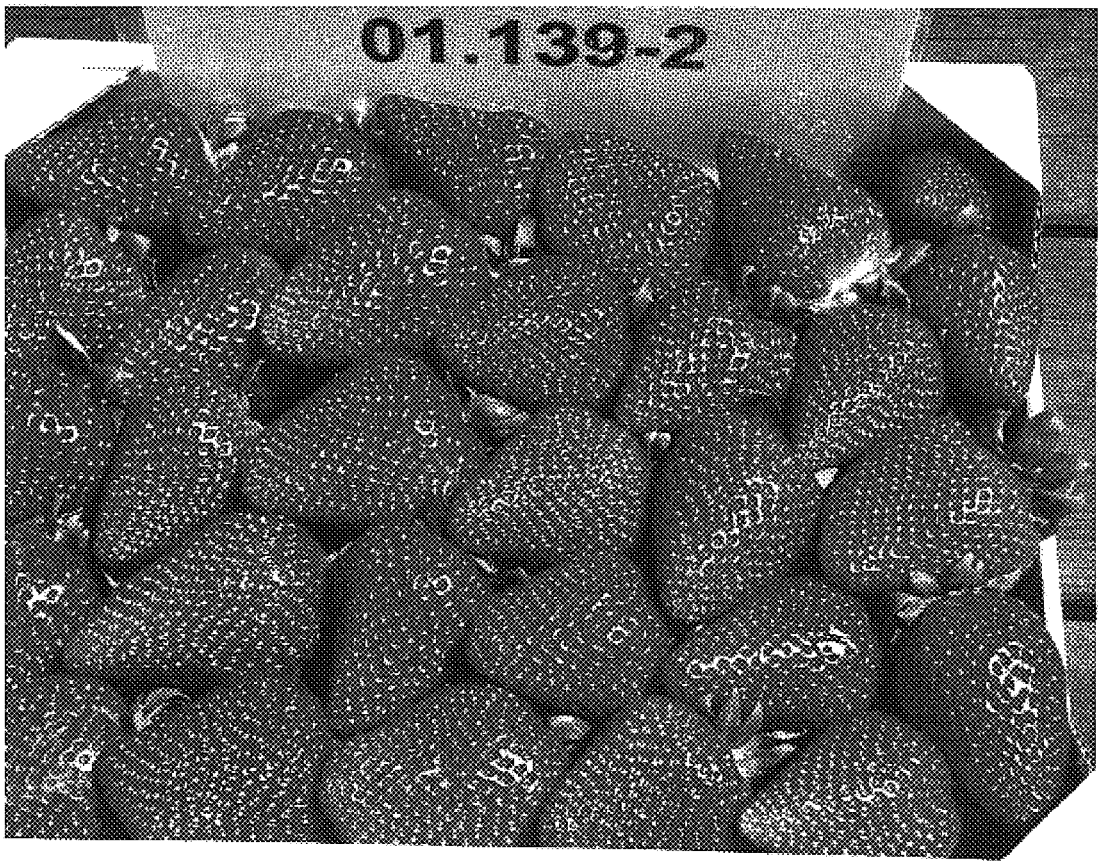
FIG. 3 shows representative mid-season fruit.

'San Andreas' is typical of day-neutral strawberry cultivars and produces fruit regardless of day length when treated appropriately in and, subtropical climates. 'San Andreas' is moderate to weak in expressing the day-neutral character, being comparable in flowering response to 'Diamante' (U.S. Plant Pat. No. 10,435) and 'Albion' (U.S. Plant Pat. No. 16,228), and less so than 'Fern' (U.S. Plant Pat. No. 5,267) or 'Irvine' (U.S. Plant Pat. No. 7,172). The production pattern for 'San Andreas' is similar to that for 'Albion'. 'San Andreas' will be of special interest for winter plantings and in summer plantings where 'Diamante' and 'Albion' have been successful.

Plants and foliage:
Fruiting plants of 'San Andreas' are similar in morphology to 'Diamante' and 'Albion' although somewhat larger early in the season. 'San Andreas' plants are similar in appearance to plants of 'Aromas', but more compact and smaller throughout the season. Comparative statistics for foliar characters near mid-season are given for 'San Andreas' and the three comparison cultivars in Table I. Individual leaflets for 'San Andreas' are similar in shape and size to the comparison cultivars, but are somewhat longer than broad, and less rounded. Leaves (including petioles) for 'San Andreas' are longer than those for 'Diamante' and 'Albion', mostly due to greater petiole length. Petioles are generally thinner than those of the comparison cultivars and tend to have heavy pubescence. The adaxial (upper) and abaxial (lower) surfaces of leaves for 'San Andreas' are similar in color to the comparison cultivars at mid season, but slightly darker early in the season. Leaves of 'San Andreas' have similar concavity to 'Aromas', 'Diamante', and 'Albion'.

Disease and pest reaction:

'San Andreas' is moderately resistant to powdery mildew (*Sphaerotheca macularis*), Anthracnose crown rot (*Colletotrichum acutatum*), Verticillium wilt (*Verticillium dahliae*), Phytophthora crown rot (*Phytophthora cactorum*) and common leaf spot (*Ramularia tulasnei*) (Table 3). When treated properly, it has tolerance to two-spotted spider mites (*Tetranychus urticae*) equal to that for the comparison cultivars. 'San Andreas' is tolerant to strawberry viruses encountered in California.

TABLE 1

Foliar and plant characteristics for 'San Andreas', 'Aromas', 'Diamante', and 'Albion'.

| Foliar Character | Cultivar 'Aromas' | 'Diamante' | 'Albion' | 'San Andreas' |
|---|---|---|---|---|
| Plant height (mm) | | | | |
| mean | 272 | 220 | 223 | 250 |
| range | 240-300 | 190-240 | 170-290 | 210-290 |
| Plant spread (mm) | | | | |
| mean | 323 | 316 | 295 | 323 |
| range | 300-360 | 265-385 | 270-315 | 300-340 |
| Mid-tier leaflet Length (mm) | | | | |
| mean | 79 | 78 | 70 | 75 |
| range | 70-90 | 60-90 | 60-80 | 70-90 |
| Width (mm) | | | | |
| mean | 74 | 77 | 68 | 69 |
| range | 70-80 | 55-90 | 60-80 | 60-80 |
| Mid-tier leaf Length (mm) | | | | |
| mean | 113 | 99 | 99 | 114 |
| range | 100-120 | 80-120 | 90-110 | 90-160 |
| Width (mm) | | | | |
| mean | 135 | 134 | 122 | 117 |
| range | 120-150 | 90-150 | 105-135 | 100-140 |
| Leaf components | | | | |
| Petiole length (mm) | | | | |
| mean | 174 | 114 | 122 | 164 |
| range | 140-210 | 100-130 | 95-180 | 130-200 |
| Petiole diameter (mm) | | | | |
| mean | 4.5 | 5.2 | 4.9 | 4.0 |
| range | 4-6 | 4-7 | 4-6 | 3-5 |
| Petiolule length (mm) | | | | |
| mean | 6.6 | 5.2 | 6.7 | 5.4 |
| range | 4.3-7.5 | 4.0-7.6 | 5.0-8.0 | 3-8 |
| # leaflets/leaf | 3 | 3 | 3 | 3 |
| Leaf convexity | some flat, most slight concave | some flat, most slight concave | some flat, most slight concave | some flat, most slight concave |
| Serrations | | | | |
| number/leaf | 19.9 | 20.2 | 23.3 | 20.8 |
| range | 16-24 | 16-24 | 21-27 | 18-24 |

TABLE 1-continued

Foliar and plant characteristics for 'San Andreas', 'Aromas', 'Diamante', and 'Albion'.

| Foliar Character | Cultivar 'Aromas' | 'Diamante' | 'Albion' | 'San Andreas' |
|---|---|---|---|---|
| shape | rounded to semi-pointed | rounded to semi-pointed | semi-pointed | semi-pointed |
| Leaf pubescence | moderate | moderate-heavy | moderate | moderate-heavy |
| Petiole pubescence density | Moderate-heavy | heavy | heavy | heavy |
| direction | perpendicular | perpendicular | perpendicular | perpendicular |
| Petiole color (Munsell) | 5 GY 8/8 | 7.5 GY 9/4 | 5 GY 8/8 | 5 GY 8/8 |
| Stipule length (mm) | | | | |
| mean | 34.2 | 31.6 | 32.5 | 32.8 |
| range | 30-39 | 22-36 | 24-37 | 18-42 |
| Stipule color | | | | |
| core | 7.5 GY 8/7 | 7.5 GY 8/7 | 5 GY 8/7 | 7.5 GY 8/7 |
| margins | 2.5 GY 9/3 | 5 GY 6/8 | 5 GY 6/8 | 7.5 GY 6/8 |
| Stolon base diameter (mm) | 3.0 | 3.2 | 3.0 | 3.0 |
| Stolons per nursery mother plant | 33.0 | 29.0 | 26.9 | 28.4 |
| Venation | | | | |
| pattern | pinnate | pinnate | pinnate | pinnate |
| color | 2.5 GY 5/5 | 10 GY 5/5 | 2.5 GY 6/8 | 2.5 Y 6/8 |

Flowering, fruiting, fruit, and production characteristics:

'San Andreas' is similar to other California day-neutral cultivars (e. g. 'Diamante' and 'Albion') in that it will flower independently of day length, given appropriate temperature and horticultural conditions. Comparative statistics for flower and fruit characters near mid-season are given for 'San Andreas' and the three cultivars in Table 4. The primary flowers for 'San Andreas' are slightly larger than those of the comparison cultivars with a calyx that is distinctly larger than the corolla on primary fruit. The sepals are similar in length and shape to those of the comparison cultivars. The calyx for 'San Andreas' varies in position but is usually more reflexed than for 'Aromas' or 'Diamante', similar to that of 'Albion'. The fruit shape for 'San Andreas' can vary, but is typically a medium to long and highly symmetrical conic. It is easily distinguished by fruit shape from 'Aromas' (shortened and rounded conic), 'Diamante' (usually a flat conic) or 'Albion' (long conic). 'San Andreas' usually has a greater proportion of symmetrical fruit than the comparison cultivars, especially early in the fruiting season. External fruit color for 'San Andreas' is slightly lighter than 'Aromas' or 'Albion', distinctly darker than for 'Diamante'. Internal color is somewhat darker with greater red pigment than for the comparison cultivars (Table 2). Achenes vary from yellow to dark red, but are usually red, and range from even with the fruit surface to slightly indented.

'San Andreas' has been tested under a variety of cultural regimes, and optimal performance is obtained when nursery treatments and nutritional programs similar to those for 'Albion', 'Diamante', and 'Aromas' are used. In general, 'San Andreas' is more vigorous than the comparison cultivars and is less sensitive to low chilling. 'San Andreas' retains excellent fruit quality in summer planting systems.

When treated with appropriate planting regimes, 'San Andreas' has larger fruit and produces greater individual-plant yield than any of the comparison cultivars (Table 5). 'San Andreas' has a similar production pattern to 'Albion' with most cultural treatments, although it is substantially more adapted to early-season winter planting. Commercial appearance ratings have been substantially higher than those for all of the comparison cultivars, especially 'Aromas'. These superior appearance scores translate directly into a larger fraction of marketable fruit than is produced by the comparison cultivars. Fruit for 'San Andreas' is substantially firmer than fruit from 'Aromas', similar in firmness to the other comparison cultivars. Subjectively, 'San Andreas' has outstanding flavor very similar to that of 'Albion'. The fruit will be exceptional for both fresh market and processing, and will be useful for home garden purposes.

TABLE 2

Foliar and fruit color characteristics for 'San Andreas' and three comparison cultivars

| Color Character | Cultivar 'Aromas' | 'Diamante' | 'Albion' | 'San Andreas' |
|---|---|---|---|---|
| Leaf color (CIELAB) Adaxial | | | | |
| L* | | | | |
| mean | 35.1 | 34.8 | 34.7 | 33.4 |
| range | 32.7-37.7 | 32.6-36.8 | 32.8-36.7 | 28.1-36.0 |
| a* | | | | |
| mean | −10.6 | −10.4 | −9.8 | −9.1 |
| range | −82--14.0 | −8.7--11.9 | −9.4--11.3 | −8.6--10.0 |
| b* | | | | |
| mean | 13.8 | 13.8 | 12.8 | 11.7 |
| range | 11.2-18.1 | 12.2-16.6 | 10.7-15.6 | 10.4-13.8 |
| Munsell | 7.5 GY 4/4 | 5 GY 4/3 | 5 GY 4/3 | 2.5 GY 4/3 |
| Abaxial | | | | |
| L* | | | | |
| mean | 52.4 | 51.1 | 50.6 | 50.2 |
| range | 50.6-54.1 | 49.7-52.2 | 43.7-53.1 | 47.8-52.8 |
| a* | | | | |
| mean | −11.6 | −12.8 | −12.4 | −12.5 |
| range | −10.7--13.6 | −11.6--14.9 | −8.6--11.4 | −12.0--12.9 |
| b* | | | | |
| mean | 17.3 | 19.5 | 17.2 | 18.5 |
| range | 14.3-23.2 | 15.3-23.5 | 14.5-19.6 | 17.3-21.5 |
| Munsell | 10 GY 7/8 | 7.5 GY 6/8 | 7.5 GY 8/7 | 5 GY 5/6 |
| Fruit color (CIELAB) | | | | |
| External | | | | |
| L* | | | | |
| mean | 34.2 | 40.8 | 36.5 | 36.0 |
| range | 31.2-38.3 | 35.5-45.4 | 32.8-40.1 | 31.8-39.4 |
| a* | | | | |
| mean | 33.9 | 36.7 | 33.3 | 36.0 |
| range | 31.5-38.6 | 35.6-40.2 | 28.3-36.2 | 34.9-43.6 |
| b* | | | | |
| mean | 14.1 | 21.2 | 17.6 | 18.4 |
| range | 9.1-16.5 | 18.8-25.7 | 12.2-24.9 | 13.2-22.9 |
| Munsell | 2.5 R 4/10 | 5 R 5/13 | 5 R 3/7 | 5 R 4/12 |
| Internal | | | | |
| L* | | | | |
| mean | 61.6 | 65.6 | 57.9 | 59.0 |
| range | 59.5-67.7 | 58.8-67.2 | 43.3-62.9 | 53.2-60.3 |

TABLE 2-continued

Foliar and fruit color characteristics for 'San Andreas' and three comparison cultivars

| Color Character | Cultivar 'Aromas' | 'Diamante' | 'Albion' | 'San Andreas' |
|---|---|---|---|---|
| a* | | | | |
| mean | 14.7 | 5.6 | 19.0 | 23.3 |
| range | 7.6-19.2 | 3.0-9.5 | 7.9-27.7 | 19.3-31.2 |
| b* | | | | |
| mean | 20.2 | 15.8 | 21.0 | 24.4 |
| range | 16.1-22.5 | 14.5-18.2 | 13.2-27.2 | 18.5-28.9 |
| Munsell | 5 R 6/11 | 10 R 7/9 | 7.5 R 4/11 | 7.5 R 5/13 |
| Achene color Munsell | 7.5 R 4/11 | 7.5 R 4/11 | 10 R 5/6 | 5 R 3/7 |

*CIELAB is the abbreviation of the international color system known as "Commission Internationale De L'Eclairage" 1978. For recommendations concerning uniform color spaces, color difference equations, and psychometric color terms, see Supplement No. 2 of CIE Publication No. 15, Paris.

TABLE 3

Disease resistance scores for 'San Andreas' and three comparison cultivars; *Phytophthora* and *Verticillium* scores were obtained in evaluations conducted in 2004-2006, *Colletotrichum* was evaluated in 2005-2006.

| Genotype | *Phytophthora* Resistance Score (5 = best) | *Verticillium* Resistance Score (5 = best) | *Colletotrichum* Resistance Score (5 = best |
|---|---|---|---|
| 'Aromas' | 4.0 | 4.5 | 2.4 |
| 'Diamante' | 2.0 | 2.8 | 2.6 |
| 'Albion' | 4.3 | 3.8 | 3.1 |
| 'San Andreas' | 3.8 | 3.8 | 2.8 |

TABLE 4

Flower and fruit characters for 'San Andreas' and three comparison cultivars.

| Character | Cultivar 'Aromas' | 'Diamante' | 'Albion' | 'San Andreas' |
|---|---|---|---|---|
| Petal number | | | | |
| mean | 5.5 | 5.4 | 5.6 | 6.6 |
| range | 5-7 | 5-6 | 5-7 | 5-7 |
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 10.1 | 9.2 | 9.6 | 11.7 |
| range | 8-11 | 7-13 | 8-11 | 9-14 |
| Petal width (mm) | | | | |
| mean | 11.8 | 10.6 | 9.0 | 12.8 |
| range | 10-13 | 10-13 | 7-10 | 11-14 |

TABLE 4-continued

Flower and fruit characters for 'San Andreas' and three comparison cultivars.

| Character | Cultivar 'Aromas' | 'Diamante' | 'Albion' | 'San Andreas' |
|---|---|---|---|---|
| Flower position (relative to foliage) | most even some exposed | most even some internal and exposed | most exposed, some even | most exposed, some even |
| Calyx diam. (mm) | | | | |
| mean | 31.3 | 32.0 | 37.5 | 37.5 |
| range | 28-33 | 25-41 | 31-48 | 34-45 |
| Corolla diam. (mm) | | | | |
| mean | 31.2 | 23.9 | 27.8 | 34.4 |
| range | 26-35 | 18-31 | 23-33 | 27-44 |
| Sepal length (mm) | | | | |
| mean | 12.3 | 12.1 | 14.1 | 13.2 |
| range | 8-15 | 10-15 | 11-18 | 11-16 |
| Sepal width (mm) | | | | |
| mean | 6.4 | 6.7 | 6.6 | 8.0 |
| range | 3-9 | 5-9 | 4-10 | 6-10 |
| Sepal color (Munsell) | 7.5 GY 6/8 | 5 GY 5/6 | 2.5 GY 6/8 | 7.5 GY 6/8 |
| Pedicel length (mm) | | | | |
| mean | 172 | 140 | 218 | 221 |
| range | 112-230 | 110-165 | 180-270 | 200-240 |
| Pedicel diameter (mm) | | | | |
| mean | 4.4 | 5.3 | 3.1 | 3.7 |
| range | 4-6 | 4-6 | 2-4 | 3-5 |
| Pedicel color | 5 GY 6/8 | 5 GY 7/10 | 5 GY 6/8 | 7.5 GY 6/8 |
| Fruit shape | | | | |
| Fruit length (mm) | | | | |
| mean | 46.6 | 46.4 | 61.7 | 58.0 |
| range | 42-52 | 39-50 | 50-76 | 46-68 |
| Fruit width (mm) | | | | |
| mean | 39.4 | 40.7 | 46.6 | 44.3 |
| range | 37-43 | 38-46 | 37-52 | 40-48 |
| Length/width | | | | |
| ratio | 1.2 | 1.1 | 1.3 | 1.3 |
| range | 1.0-1.4 | 1.0-1.2 | 1.2-1.5 | 1.1-1.4 |
| subjective | mostly medium to | rounded to flat conic | most long symmetrical | medium-long symmetrical |

TABLE 4-continued

Flower and fruit characters for 'San Andreas' and three comparison cultivars.

| Character | Cultivar 'Aromas' | 'Diamante' | 'Albion' | 'San Andreas' |
|---|---|---|---|---|
| | short flat conic | | conic | conic |
| Primary/ secondary fruit comparison | | | | |
| size (subjective) | 60-80% | 60-80% | 60-70% | 60-80% |
| shape | similar shape | similar shape | similar shape | similar shape |
| Extent/size of hollow core | small-absent | small-absent | small-medium | Medium |
| Calyx | | | | |
| position | indented-even with neck | even-indented | even-reflexed | often reflexed |
| size relative to fruit | equal or greater than fruit diameter | equal or greater than fruit diameter | equal or greater than fruit diameter | equal or greater than fruit diameter |
| Seed position | indented-extruded | indented-even | indented-extruded | indented-slightly extruded |
| Adherence of Calyx to Fruit | intermediate | intermediate | intermediate | intermediate |

Flower measurements and fruit measurements obtained May 9Jun. 6, 2006. Subjective observations obtained Jul. 31, 2006.

TABLE 5

Performance 'San Andreas'and three comparison cultivars evaluated at the Watsonville Research Facility in 2005-7. All plants for these trials were harvested from a commercial nursery near Macdoel, CA on October 15-16, and transplanted after 18-21 days supplemental storage. Fruit harvest was initiated in early April and continued through the first week of October. (52" 2-row beds, 17,300 plants/acre).

| Item | Yield (g/plant) | Appearance Score (5 = best) | Fruit Size (g/fruit) | Firmness |
|---|---|---|---|---|
| 'Aromas' | 3,108 | 3.1 | 27.0 | 9.6 |
| 'Diamante' | 2,653 | 3.5 | 31.2 | 11.0 |
| 'Albion' | 2,461 | 3.9 | 30.5 | 11.1 |
| 'San Andreas' | 3,293 | 4.4 | 31.6 | 11.5 |

What is claimed is:

1. A new and distinct cultivar of strawberry plant having the characteristics substantially as described and illustrated herein.

* * * * *

UNITED STATES PATENT AND TRADEMARK OFFICE

CERTIFICATE OF CORRECTION

PATENT NO. : PP 19,975 P2
APPLICATION NO. : 12/011335
DATED : May 12, 2009
INVENTOR(S) : Shaw and Larson It is certified that error appears in the above-identified patent and that said Letters Patent is hereby corrected as shown below:

Column 2 of "Detailed Description of the Invention", at line 10, please replace "appropriately in and, subtropical climates" with --appropriately in arid, subtropical climates--;

Column 8, between Tables 4 and 5, please replace "May9Jun.6, 2006." with --May 9-Jun. 6, 2006.--

Signed and Sealed this

First Day of September, 2009

David J. Kappos

David J. Kappos
*Director of the United States Patent and Trademark Office*